United States Patent [19]

Tator et al.

[11] Patent Number: 4,698,507

[45] Date of Patent: Oct. 6, 1987

[54] ENVIRONMENTAL EXPOSURE TESTER

[75] Inventors: Kenneth B. Tator, Coraopolis; Richard O. Lackey, Mars, both of Pa.

[73] Assignee: KTA-Tator, Inc., Pittsburgh, Pa.

[21] Appl. No.: 912,570

[22] Filed: Sep. 26, 1986

[51] Int. Cl.[4] .............. G01N 21/01; G01N 25/00
[52] U.S. Cl. .................... 250/429; 73/150 R; 250/432 R; 250/433; 374/7; 374/57
[58] Field of Search ............ 374/7, 57; 250/504 R, 250/443.1, 454.1, 455.1, 429; 73/150 R

[56] References Cited

U.S. PATENT DOCUMENTS

| | | | |
|---|---|---|---|
| 1,458,941 | 6/1923 | Jameson | 73/150 R |
| 1,558,786 | 10/1925 | Buttolph | 73/150 R |
| 1,818,687 | 8/1931 | Buttolph | 73/150 R |
| 1,870,512 | 8/1932 | Jameson | 73/150 R |
| 1,969,606 | 8/1934 | Hall | 73/150 R |
| 2,195,726 | 4/1940 | Jameson | 73/150 R |
| 2,434,450 | 1/1948 | Williford | 73/150 R |
| 2,732,501 | 1/1956 | Blaeker | 250/429 |
| 2,804,770 | 9/1957 | Günther et al. | 73/150 R |
| 2,822,476 | 2/1958 | Osgood | 250/455.1 |
| 2,945,417 | 7/1960 | Caryl et al. | 73/150 R |
| 2,987,914 | 6/1961 | Günther et al. | 73/150 R |
| 3,116,977 | 1/1964 | Grabowski et al. | 422/53 |
| 3,224,266 | 12/1965 | Klippert | 73/150 R |
| 3,266,306 | 8/1966 | Arnold et al. | 73/150 R |
| 3,267,738 | 8/1966 | Korn, Jr. | 73/150 R |
| 3,327,536 | 6/1967 | Fitzgerald | 73/150 R |
| 3,353,025 | 11/1967 | Sturm | 73/150 R |
| 3,426,590 | 2/1969 | Suga | 73/150 R |
| 3,500,682 | 3/1970 | Newfield | 73/150 R |
| 3,501,942 | 3/1970 | Fitzgerald et al. | 374/57 |
| 3,576,125 | 4/1971 | Kockott et al. | 374/57 |
| 3,582,282 | 6/1971 | Kämpf et al. | 73/150 R |
| 3,664,188 | 5/1972 | Kockott | 73/150 R |
| 3,685,969 | 8/1972 | Young, III | 422/53 |
| 3,686,940 | 8/1972 | Kockott | 73/150 R |
| 3,886,791 | 6/1975 | Grossman | 73/150 R |
| 3,889,531 | 6/1975 | Suga | 73/150 R |
| 3,936,273 | 2/1976 | Powell | 422/53 |
| 4,012,954 | 3/1977 | Klippert | 73/150 R |
| 4,019,062 | 4/1977 | Rongren | 250/504 R X |
| 4,069,019 | 1/1978 | Suga | 422/53 |
| 4,092,122 | 5/1978 | Suga | 422/53 |
| 4,101,424 | 7/1978 | Schooley et al. | 250/504 R |
| 4,282,181 | 8/1981 | Pierce | 422/53 |
| 4,391,522 | 7/1983 | Schmid et al. | 73/150 R |
| 4,517,893 | 5/1985 | Wile et al. | 250/504 R |
| 4,644,899 | 2/1987 | Glaus | 250/504 R |

Primary Examiner—Daniel M. Yasich
Attorney, Agent, or Firm—Harry D. Anspon

[57] ABSTRACT

Materials to be tested for resistance of immersion swelling, drying shrinkage, thermal expansion and thermal contraction under light exposure are placed on a mount on a rotating shaft which immerses the sample in water, heats and dries it, and exposes it to light before cooling it by again immersing it in water. The samples may be simultaneously exposed to air pollutants by adding gases to a corrosion resistant chamber enclosing the rotating shaft. The chamber enclosing the rotating samples is composed of a lower tank base and a cover fitting into a liquid seal well on the tank base. The cover is fitted with fluorescent lights, an infrared heating strip, a thermocouple and a viewing port. A controller with indicator for the radiant heating strip and a speed control on the rotating shaft drive motor together with "run" and "pause" controls permit selection of the exposure cycles and their conditions. The aqueous test liquid in the tank base is maintained at a constant temperature by fluid flow through a heat exchanger using a thermocouple and controller.

10 Claims, 19 Drawing Figures

ENVIRONMENTAL EXPOSURE TESTER

BACKGROUND OF THE INVENTION

1. Field of the Invention

The integrity of materials is well known to be affected by their environmental exposure. Testing apparatus has been designed to simulate environmental exposure. Numerous testers incorporate various light exposure devices to examine the degradation of materials by exposure to light, particularly ultraviolet light. Some of these testers also incorporate sprays or fogs, whereby the surfaces of the samples undergoing light exposure are wetted and allowed to dry as part of the cycle of testing along with light exposure. Most of such testers limit the extent of heating of the sample undergoing light exposure and moisture exposure, although limited sample heating is practiced in several testers. A few testers employ sample immersion as part of a test cycle with or without light exposures. Among immersion testers are several testing corrosion resistance of metals by immersion in a corrosive environment.

The light stability testers often are complex instruments designed to provide and/or monitor light of selected wavelengths for the testing.

Despite the number and variety of testers, there is no simple tester which subjects materials to the severe conditions which the environment sometimes imposes on materials.

These severe conditions are those encountered when the combination of conditions is such that the materials being tested are subjected to test influences which accentuate flaws in the performance of sample materials.

It has been found that these severe conditions are obtained when light exposure of the samples also includes alternate heat exposure and cooling while the sample also is undergoing intermittent prolonged water immersion followed by drying during heat and light exposure. The water immersion often includes immersion in water containing salts which accelerate metallic corrosion. In addition, the drying step in the gas phase often includes gaseous contaminates which accelerate metallic corrosion and/or which affect the strength of materials such as plastics.

This invention describes a simple tester which subjects samples to a combination of environmental exposures, including ultraviolet light, while a sample is being heated and cooled to cause material expansion and contraction while the sample also is undergoing prolonged water immersion followed by drying. The water frequently contains contaminants such as salts and hydrocarbon oils, and the gas phase also may contain contaminants such as gases present in polluted environments, including sulfur oxides, nitrogen oxides, oxides of carbon, ammonia, hydrogen sulfide, hydrocarbons and their oxidation products, halogens, halogenated hydrocarbons and their oxidation products. Where the material being tested is employed in a plant environment, the aqueous test liquid and the gas phase may contain other contaminants associated with a particular plant.

This invention is a device for measuring and testing the performance of a variety of coating materials including their ability to provide corrosion resistance while being subjected to environmental conditions including ultraviolet light, heating and cooling with associated expansion and contraction, immersion in water followed by drying, and exposure to chemicals in the water liquid phase as well as the gas phase including the effect of heat and water in the presence of these chemicals and in the presence of ultraviolet light.

While this invention is useful in testing all manner of coatings such as paints, lacquers, inks and primers on specified substrates, it also is useful in testing plastics, coated and uncoated textiles, rubbers and rubber coatings, packaging materials, as well as coated and uncoated metals, coated and uncoated woods, and adhesives for plastics, rubbers, metal, and wood products, and composite structures such as fiberglass reinforced plastics.

In the test apparatus of this invention, the combined effects of ultraviolet light, thermal expansion and contraction, water immersion, leaching and swelling are followed by heating to cause drying shrinkage in the presence of a corrosive vapor phase after immersion in a corrosive liquid phase. The light exposure is made so that it is accelerated by heat, and, with these effects acting in concert, failures are caused to appear in coatings, rubbers, plastics and adhesives. The results of these combined stringent conditions acting upon the samples establish performance ratings for the samples.

2. Description of the Related Art

The testing apparatus of the prior art for coatings and for corrosion resistance is listed in the following table:

| U.S. Pat. No. | Date  | Name            |
|---------------|-------|-----------------|
| 1,458,941     | 6/23  | Jameson         |
| 1,558,786     | 10/25 | Buttolph        |
| 1,818,687     | 8/31  | Buttolph        |
| 1,870,512     | 8/32  | Jameson         |
| 1,969,606     | 8/34  | Hall            |
| 2,195,726     | 4/40  | Jameson         |
| 2,434,450     | 1/48  | Williford       |
| 2,804,770     | 9/57  | Gunther et al.  |
| 2,945,417     | 7/60  | Caryl et al.    |
| 2,987,914     | 6/61  | Gunther et al.  |
| 3,116,977     | 1/64  | Grabowski et al.|
| 3,224,266     | 12/65 | Klippert        |
| 3,266,306     | 8/66  | Arnold et al.   |
| 3,267,738     | 8/66  | Korn, Jr.       |
| 3,327,536     | 6/67  | Fitzgerald      |
| 3,353,025     | 11/67 | Sturm           |
| 3,426,590     | 2/69  | Suga            |
| 3,500,682     | 3/70  | Newfield        |
| 3,501,942     | 3/70  | Fitzgerald et al.|
| 3,576,125     | 4/71  | Kockott         |
| 3,582,282     | 6/71  | Kampf et al.    |
| 3,664,188     | 5/72  | Kockott         |
| 3,685,969     | 8/72  | Young III       |
| 3,686,940     | 8/72  | Kockott         |
| 3,886,791     | 6/75  | Grossman        |
| 3,889,531     | 6/75  | Suga            |
| 3,936,273     | 2/76  | Powell          |
| 4,012,954     | 3/77  | Klippert        |
| 4,069,019     | 1/78  | Suga            |
| 4,092,122     | 5/78  | Suga            |
| 4,282,181     | 8/81  | Pierce          |
| 4,391,522     | 7/83  | Schmid et al.   |

Brief comments about the exposure conditions of each prior art apparatus are included below, along with information on how the conditions employed differ from the teachings of the present invention:

U.S. Pat. No. 1,458,941 exposes samples to ultraviolet light from an electric lamp while cooling the samples with air flow and evaporative cooling. Heating of samples during light exposure is avoided, and there is no water immersion of samples.

U.S. Pat. No. 1,558,786 exposes samples to ultraviolet light with air flow and humidity controlled by baffles, samples are not exposed to heat, nor are they immersed in water.

U.S. Pat. No. 1,818,687 exposes samples to ultraviolet light but filters out heat producing rays. Samples can be exposed to different humidity and temperatures, but they are not exposed to intermittent heating and cooling nor to elevated temperatures or immersion in water.

U.S. Pat. No. 1,870,512 describes apparatus for directing light and heat onto samples which are subject to a water spray between intervals of light exposure and which are also subject to controlled atmospheric humidity. This prior art apparatus directs spray on one surface of a sample and does not provide for sample immersion, and its light and heat rays arise from the same source and air flow is employed to cool the chamber below its set point temperature.

U.S. Pat. No. 1,969,606 discloses an apparatus which tests color materials by exposure to light under controlled humidity and temperature. The sample is not immersed, and the temperature of the sample does not cycle.

U.S. Pat. No. 2,195,726 discloses a masking device for use in connection with the testing of samples of color for fastness to light. The exposure conditions mentioned are light rays only.

U.S. Pat. No. 2,434,450 describes a sample holder for use in accelerated light testing, which holder is curved to receive equal intensity of light from a substantially point source of light. The exposure conditions described employ light rays only.

U.S. Pat. No. 2,804,770 describes apparatus for exposing samples to intermittent light exposure. The samples are not immersed, nor are they heated.

U.S. Pat. No. 2,945,417 claims an apparatus for concentrating solar rays on materials using a mirror holding frame while blowing air over the sample surfaces to remove excess heat. A sample spray system and an air humidifier are mentioned, but no sample immersion is practiced, nor is there a controllable heat source employed.

U.S. Pat. No. 2,987,914 claims an apparatus for light exposure with two zones for fluid flow to cool or heat in a preselected manner. The apparatus does not provide for sample immersion, and intermittent heating and cooling are not effected.

U.S. Pat. No. 3,116,977 discloses an apparatus to screen corrosion inhibitors by immersing metallic test specimens into a heated bath of water having the inhibitor dissolved therein, withdrawing the metallic specimens and heating them, and continuing the periodic immersion and withdrawal for a substantial period. No light exposure is provided, however, and the specimens are heated by current through the specimen plates.

U.S. Pat. No. 3,224,266 claims an apparatus for testing samples under conditions such as humidity, rain, or complete immersion in liquid, heat and air circulation, as well as light and dark periods with controlled changeover between light and dark. It provides for heating with a heater source of warm air in addition to heat from the illumination source. This prior art apparatus does not provide a separate radiant heater, and the rapid sequencing of immersion (with cooling) followed by radiant heating cannot be achieved.

U.S. Pat. No. 3,266,306 describes an apparatus to test resistance of materials to humidity by exposing them to steam pressure in a chamber. No light exposure is practiced in this prior art patent.

U.S. Pat. No. 3,267,738 discloses a test unit to expose test specimens at high altitude conditions for known periods of time and to return them to a package for ground return. No radiant heating or sample immersion is disclosed.

U.S. Pat. No. 3,327,536 describes a testing unit for large structures with ultraviolet light and infrared ray sources. While rain simulation is included, there is no immersion in water, nor are rapid intermittent heating and cooling by immersion described.

U.S. Pat. No. 3,335,025 describes an apparatus for testing samples exposed to humidity and irradiation. Capacitance is employed to measure humidity at the sample. Sample immersion and radiant heating are not described.

U.S. Pat. No. 3,426,590 discloses an apparatus for exposing samples to light wavelengths, with different proportions of light of the various wavelengths. No immersion of samples or radiant heating are described.

U.S. Pat. No. 3,500,682 describes a weathering apparatus where the samples are exposed to light and to water vapor. The samples are not immersed, nor are they heated by an infrared heater in the vapor space. Samples are placed on a stationary mount.

U.S. Pat. No. 3,501,942 claims a process for accelerating paint weathering by spray wetting with deionized water, drying with an infrared source, and exposure to ultraviolet light. The composition of the energy in ultraviolet, visible light, and infrared is defined. The process does not mention sample immersion. The copending apparatus patent has not been issued.

U.S. Pat. No. 3,576,125 claims an apparatus for uniform heat or light irradiation using end loss radiation compensators. Immersion of samples in water is not mentioned.

U.S. Pat. No. 3,582,282 describes a process for accelerating the testing of pigmented paint films by radicals produced in a gas to which the films are exposed. The radicals are formed from water vapor by a high frequency source which is not used in the present application. Radiant heating and immersion with light irradiation are not employed in this prior art patent.

U.S. Pat. No. 3,664,188 claims an apparatus to accelerate testing by exposing samples to irradiation at super ambient pressures. The present application employs a gas phase at atmospheric pressure. This prior art patent does not provide for sample immersion and heating with light exposure.

U.S. Pat. No. 3,685,969 discloses an apparatus for testing the strength of specimens under corrosive conditions. Specimens under stress are subjected to intermittent immersion using gravity flow of corrosive fluid to and from a fixed tank with the specimens. Light irradiation is not mentioned, nor is radiant heating before immersion.

U.S. Pat. No. 3,686,940 claims an apparatus for exposing test samples to ultraviolet and visible light radiation by filtering the radiations to provide for removal of infrared radiation and conducting the heat away by cooling tubes with fins. Thus, heating of samples is avoided in this prior art patent.

U.S. Pat. No. 3,886,791 describes an apparatus for providing sample exposure to light, humidity, condensation, heat and/or atmospheric pollutants. Sample immersion and the heating by infrared radiation followed by immersion cooling are not described in this prior art patent.

U.S. Pat. No. 3,889,531 discloses a weather test apparatus where samples on a transverse rotary test support receive sunlight from focused mirrors, while being cooled by air flow through the center of the transverse support. Motors with cam switches rotate the sample support 90° to provide exposure to rain as well as averaged light exposure on the four faces of the transverse support. Radiant heating of the samples followed by cooling by water immersion is not employed in this prior art patent.

U.S. Pat. No. 3,936,273 discloses an apparatus for determining the corrosion protection performance of a fluid. This apparatus rotates test specimens mounted on a shaft through the liquid and thereafter may maintain the test specimens for extended periods in the fluid prior to examination for the degree of corrosion. This prior art patent does not provide for irradiation by light or the radiant heating in the vapor space although the testing fluid bath may be cooled.

U.S. Pat. No. 4,012,954 claims an apparatus for testing light and weather-resisting properties of materials by employing a mirror reflecting infrared and passing ultraviolet and visible light from an illumination source together with a second mirror reflecting visible and ultraviolet light while transmitting the infrared portion. Samples on a horizontal support can be flooded with water, drained or water cooled, and may also be air cooled. In this prior art patent there is no infrared heater in the vapor space. Infrared heating is avoided.

U.S. Pat. No. 4,069,019 discloses an apparatus for spray corrosion testing in which the water seal groove on an open topped test tank having a lid to cover the test tank is provided with a flexible porous insert of a water absorbing material. The water seal groove of this application does not contain a flexible porous insert of a water absorbing material.

U.S. Pat. No. 4,092,122 discloses a corrosion testing machine in which specimens on a rotating annular frame receive spray from a tower at the center of a rotating column supporting the annular frame. No light expsure is provided, nor is sample immersion, nor is radiant heating in the vapor space.

U.S. Pat. No. 4,282,181 describes an apparatus for accelerated corrosion testing of parts in which the parts are lowered into a corrosive medium and then raised into a drying zone for predetermined, repetitive periods. Although infrared heating is employed, and although the test can be applied to paints, no mention of ultraviolet light exposure is made.

U.S. Pat. No. 4,391,522 claims an apparatus for determining light and weather resistance of samples, which apparatus is equipped with a radiation measuring probe to measure intensity and/or dosage in one of several pre-selected spectral regions. Radiant heating and cooling by sample immersion are not mentioned.

SUMMARY OF THE INVENTION

In summary, while patents have described apparatus capable of undertaking one or more of the separate steps which are performed in combination by the apparatus of this disclosure, none of the prior art patents has described an apparatus similar to this disclosure and which apparatus provides for sample exposure to light (particularly ultraviolet light), while providing for sample immersion in water, followed by radiant heating in the vapor space. The water employed for immersion provides for sample cooling and water absorption, while the vapor space radiant infrared heating provides for sample drying and heating. This disclosure apparatus subjects a sample to expansion and contraction by heating and cooling while at the same time subjecting the sample to swelling and shrinkage through water immersion and through radiant heat drying. These processes occur in the presence of light acting on a warmed sample in a vapor space which may contain pollutants and a water immersion bath which may contain corrosive compounds and contaminants. This combination of exposure sequences tests sample specimens under conditions which are severe enough to separate the performance of samples among a group of good coatings or materials.

The design of the apparatus is such that the closest approach to the lamps providing light exposure to the samples occurs immediately after the sample has passed the closest approach to the infrared heater. Thus, the samples are exposed to the highest intensity of ultraviolet and visible light when they are at their highest temperature. This exposure to light at an elevated temperature is a particularly severe condition. While the highest light intensity occurs at the samples' closest proximity to the lamps, the design of the chamber with its polished walls provides for multiple reflections of the emitted light so that the samples are exposed to reflected light through a large portion of their rotation, and low light levels occur only when the sample is immersed in the water bath in the position where the light is screened by the shadow of the rotating transverse shaft bearing its appended sample mounts. In this manner a sample is exposed to light while under expansion and contraction stresses caused by thermal expansion and contraction, and also by water absorption swelling causing expansion stress and by dehydration contraction causing shrinkage stress.

Since the samples employed are often coatings on metal coupons, these conditions elicit the effect of differential thermal expansion of the coating against its metallic substrate. Since immersion in water containing corrosive contaminants and exposure to a vapor space with pollutants also may be employed at the same time, the development of porosity in the coating and/or its loss of adhesion to the substrate is accelerated by these conditions. Coating permeability to pollutants also is a factor in this type of testing.

While the combination of exposure conditions possible provides the basic novelty to this apparatus, there is another factor which can be utilized to enable a user of this apparatus to design his own environmental exposure condition to emphasize time effects of exposure conditions. This factor resides in a control system which allows test specimens to be held in any given position for a time period from 1 second to 10 hours. At the same time the rotation which occurs in a given time period can be varied from a few degrees to multiple rotations. The temperature setting of the infrared heater also can be varied, and the temperature of the water bath can be varied. This flexibility allows the user to adjust his test conditions to those deemed most critical in his application.

The common immersion solutions are distilled water, fresh water, salt water, sea water, dilute acid solutions, dilute alkali solutions and anti-freeze solutions. Hydrocarbon oils also may be added to simulate oil contamination. These solutions can be maintained at temperatures from above ambient temperature to 0° or even lower when water with ethylene glycol is employed as an anti-freeze immersion solution. With the latter mixtures temperature extremes can be reached to test coatings by temperature changes from 100° C. to −30° C. The tank test liquid is maintained at a constant temperature.

Any one of a number of methods may be used to maintain the tank test liquid at a constant temperature. Most commonly, the test liquid is pumped from the tank base through external tubing in the form of a coil and returned to the tank base after traversing the coil. This coil is immersed in a separate temperature controlled bath so that the test bath liquid moving through the coiled tubing is held at a constant temperature by heat exchange through the coiled tubing. The test bath liquid temperature also can be maintained by the simple method of blowing cooling air against the bottom of the tank base as required. The test liquid temperature also can be controlled by surrounding the tank base with a liquid filled tray having rubber dams molded to fit the tank base and whose liquid in the tray is circulated to a separate temperature controlled bath. The tank base also may have its test liquid temperature controlled by attached plate coils through which plate coils is passed a temperature controlled liquid. In some instances, internal or external serpentine tubing can be attached to the tank base through which tubing is passed a temperature controlled liquid. Any suitable method of obtaining a constant temperature in the aqueous test liquid might be utilized.

The infrared heater has an adjacent and associated temperature sensing probe which controls the electrical energy input to the infrared heater. The heater commonly employed has a top temperature setting of 100° C., although higher temperature units can be obtained and employed for unusual test conditions.

Thus, with the apparatus of this disclosure, temperature variations from 100° C. to −10° C. can be tested. With modifications, temperature fluctuations from 150° C. to −30° C. can be used to test specimens.

The gases employed in the vapor phase most often are those commonly encountered in the atmosphere. These include uncontaminated air, and air containing oxides of carbon, oxides of sulfur, oxides of nitrogen, hydrogen sulfide, ammonia and/or acids such as acetic acid, hydrochloric acid and sulfuric acid (mists).

DESCRIPTION OF THE ILLUSTRATED EMBODIMENTS

Figure 1A:
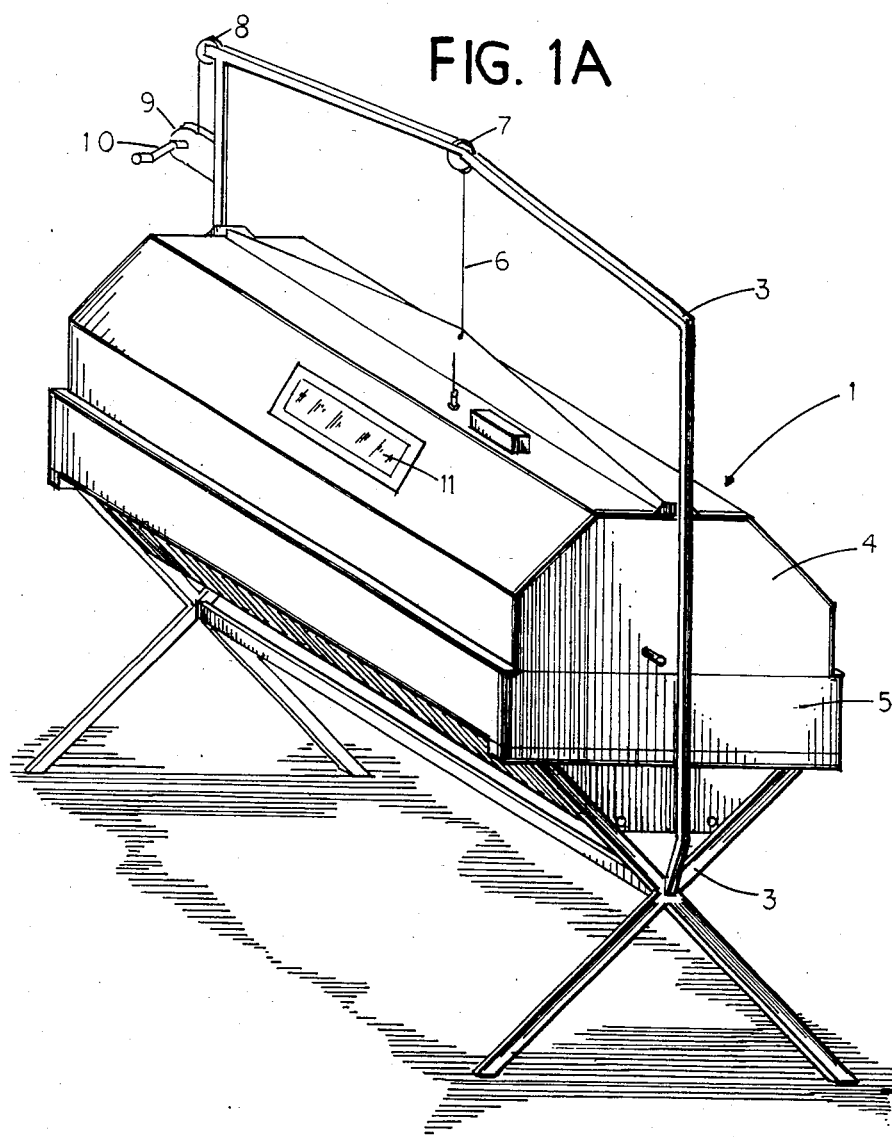
FIG. 1A shows a perspective view of the right side of the test apparatus for determining sample resistance to light, temperature changes and water immersion with cover in place.
Figure 1B:
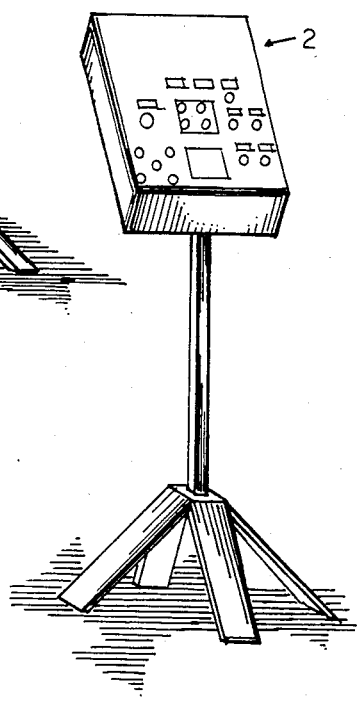
FIG. 1B shows a separate control box for the test apparatus.
Figure 1C:
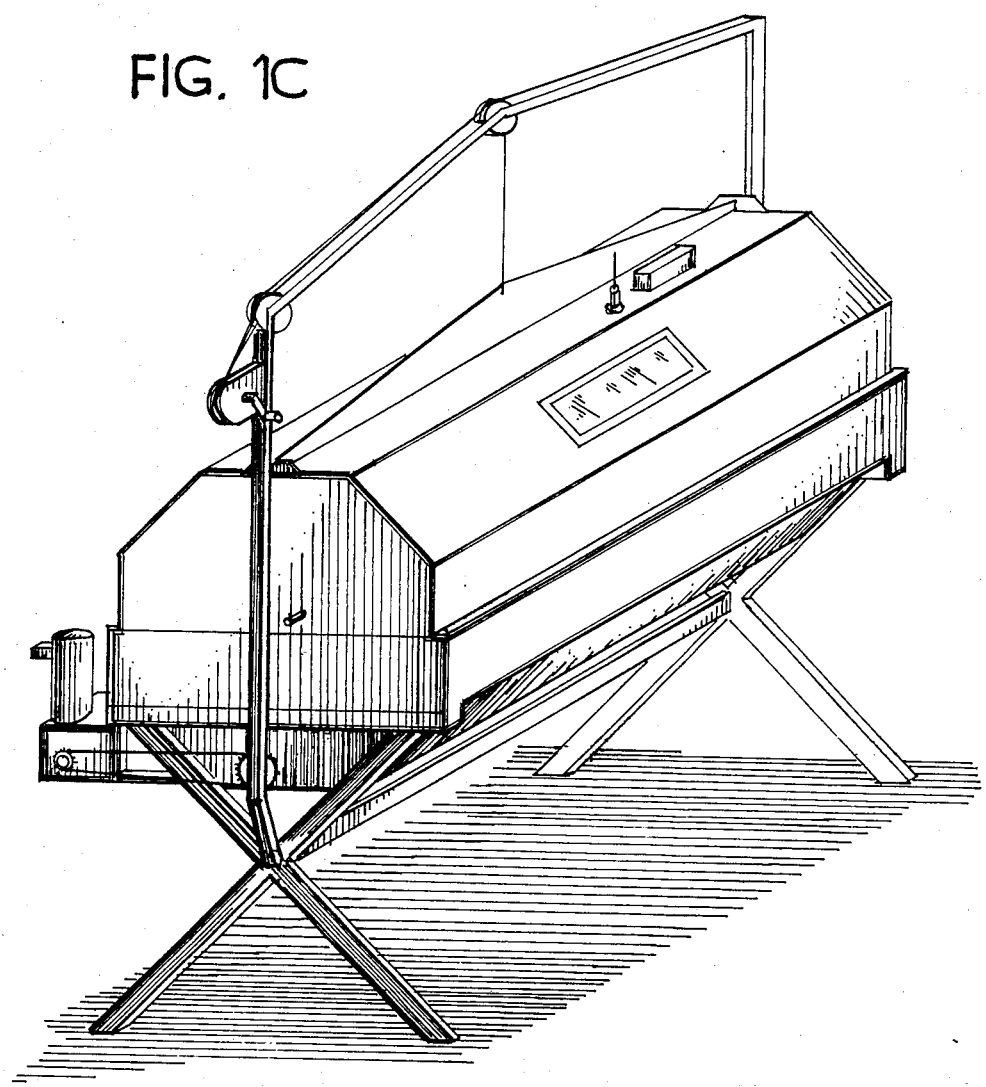
FIG. 1C shows a perspective view of the left side of the test apparatus.

In FIG. 1A the test apparatus 1 is shown in perspective from the right side. In FIG. 1B a control box 2 for the test apparatus is shown. The test apparatus 1 of FIG. 1A is composed of a support frame 3 with a moveable cover 4 and a tank base 5. The cover is supported by a wire rope 6 passing over pulleys 7 and 8 mounted on an overhead extension of the frame 3. The wire rope 6 is wound upon a winch 9 with a handle 10. Electrical cables from the control box to the cover and from the control box to the power source are not shown. A viewing port 11 on the cover 4 is shown. FIG. 1C is the test apparatus 1 viewed from the left side.

Figure 2:
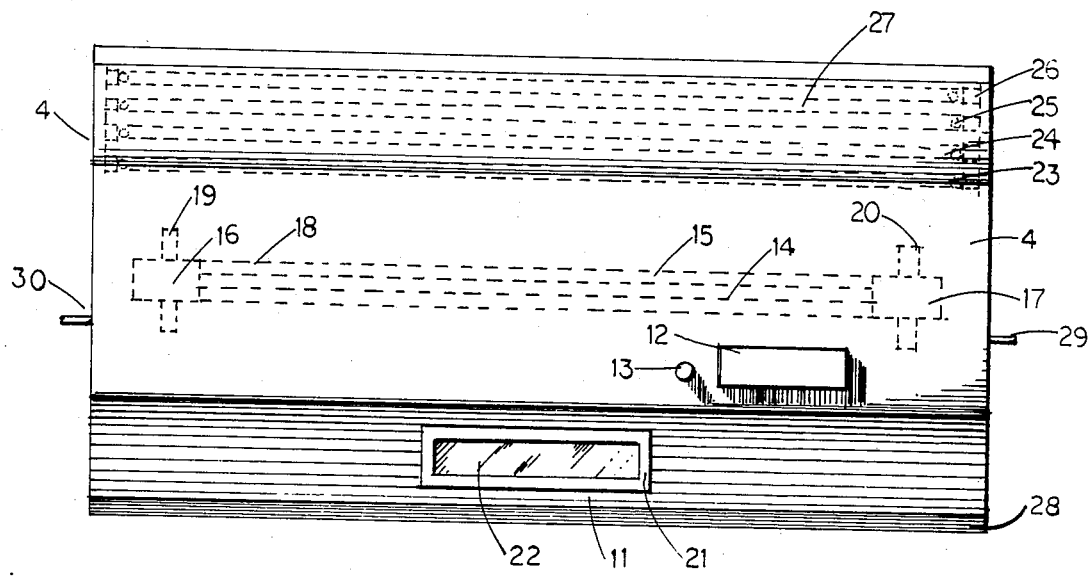
FIG. 2 is a top view of the cover of the test apparatus.

In FIG. 2, which is the top view of the moveable cover 4 of the test apparatus, the viewing port 11 is shown with junction box 12 and thermocouple 13 which is adjacent to the heater strip 14 positioned in its reflector 15. The infrared heater strip is secured in the two ends 16 and 17 of the heater unit 18 with its reflector 15. The ends 16 and 17 of the heater unit 18 are attached to mounting strips 19 and 20. The viewing port 11 is secured by mounting plate 21 with a cutout opening for the transparent panel 22. The cover 4 contains four fluorescent tubes 23, 24, 25 and 26 mounted in fluorescent tube holders supported on plate 27. The skirting shoulder 28 supports the cover when it rests on the tank base. Gas inlet and exit ports 29 and 30 allow a controlled gas phase to be maintained.

Figure 3:
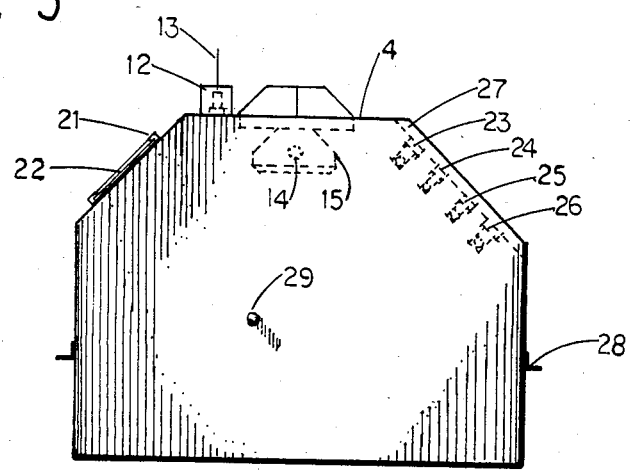
FIG. 3 is a side view of the cover of the test apparatus.

In FIG. 3 showing the side view of the moveable cover 4 the skirting shoulder 28 is shown in profile. The transparent panel 22 with its mounting plate 21 also is shown in profile. The thermocouple 13 is shown in its position adjacent to the infrared heating element 14 below the reflector 15. The fluorescent tubes 23, 24, 25 and 26 are shown in side view in their tube holders mounted on plate 27. The junction box 12 houses the electrical connections to the cables which are not shown and which lead to the control box. Gas inlet port 29 is shown.

Figure 4:
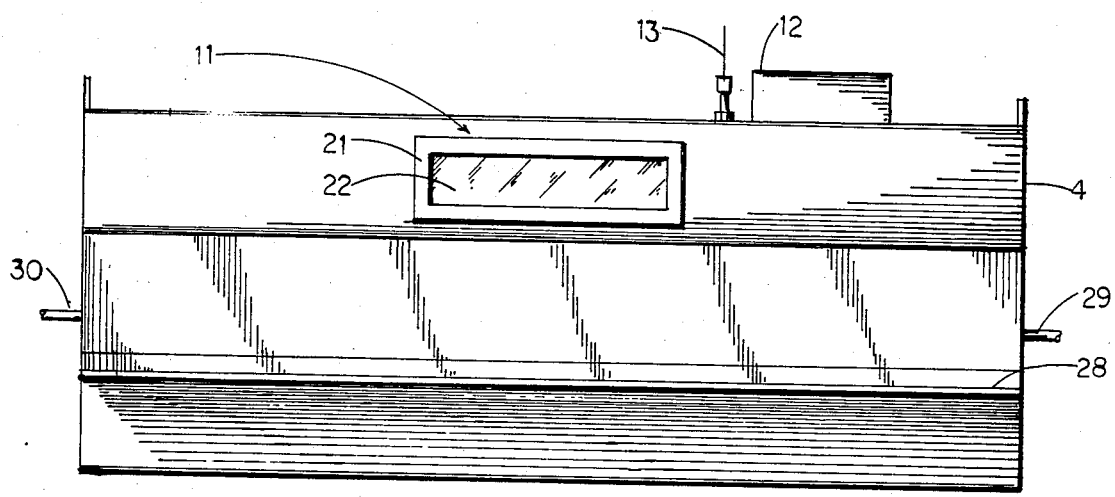
FIG. 4 is a front view of the cover of the test apparatus.

In FIG. 4 showing the front view of cover 4 the junction box 12 and thermocouple 13 are indicated with viewing port 11 and with its mounting plate 21 for the transparent panel 22. The skirting shoulder 28 supports the cover when it rests on the tank base. Electrical lines from the thermocouple 13 and the junction box 12 to the control box are not shown. Gas inlet and outlet ports 29 and 30 are shown.

Figure 5:
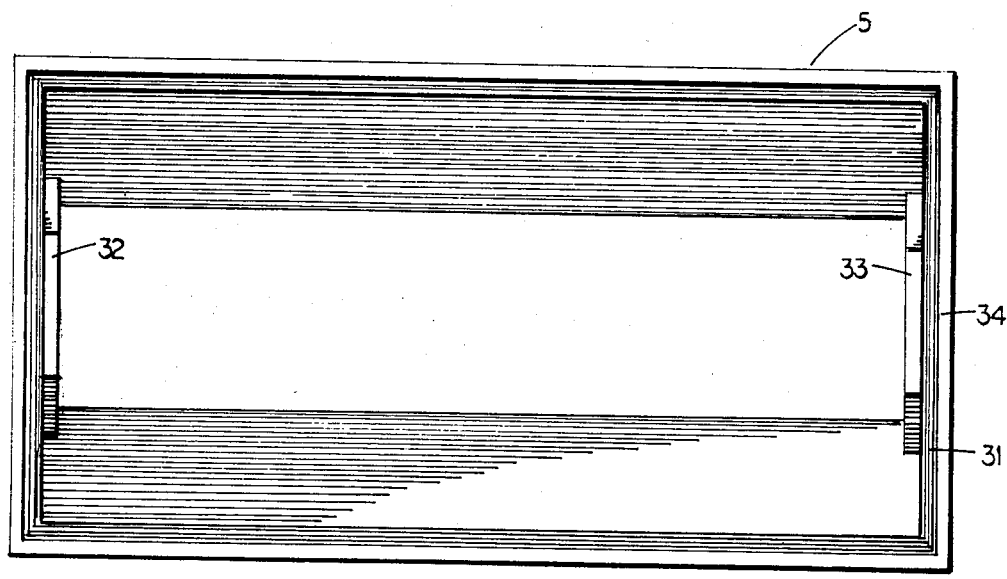
FIG. 5 is a top view of the tank base of the test apparatus.

In FIG. 5, which is a top view of the tank base 5, the recessed well 31 contains liquid which is used to provide a liquid seal for the moveable cover. The angles 32 and 33 support the bearings at the ends of the elongated shaft on which the samples are mounted. The outer rim of the well 31 is stiffened by a lip 34.

Figure 6:
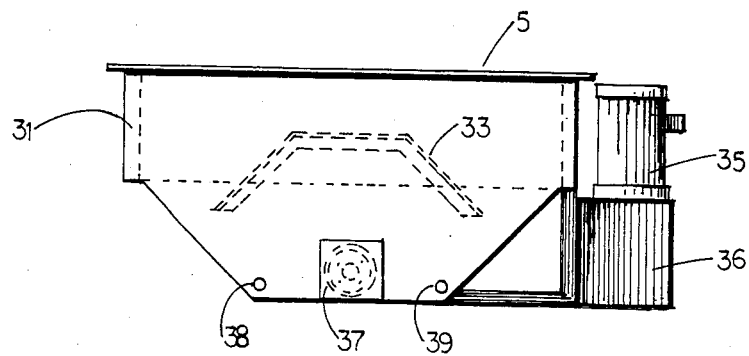
FIG. 6 is a side view of the tank base of the test apparatus.

In FIG. 6, the side view of the tank base 5, the recessed well 31 for liquid sealing is shown with the support angle 33. The drive motor 35 and its gear box 36 are outlined and also the mounting support 37 for liquid sealing bearing. Tank filling hole 38 and tank drain hole 39 are also shown.

Figure 7:
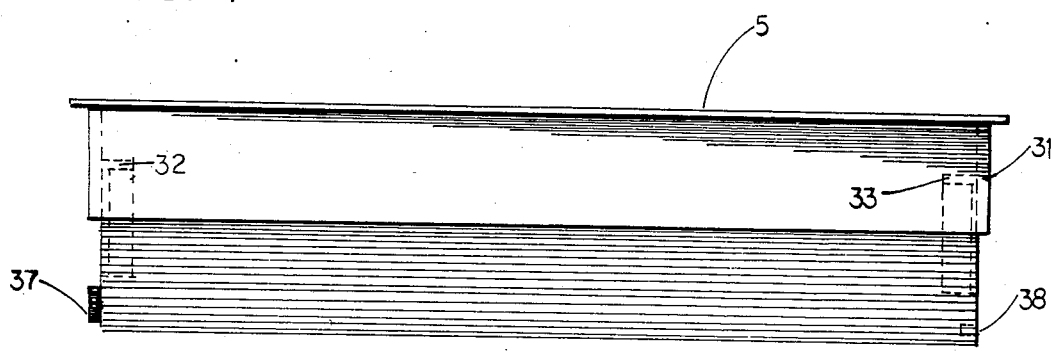
FIG. 7 is a front view of the tank base of the test apparatus.

In FIG. 7, the front view of the tank base 5, the supports 32 and 33 for bearings of the elongated shaft holding the samples are shown and the recessed well 31 for liquid sealing. The mounting support 37 for the liquid sealing bearing is indicated as is the tank filing hole 38.

Figure 8:
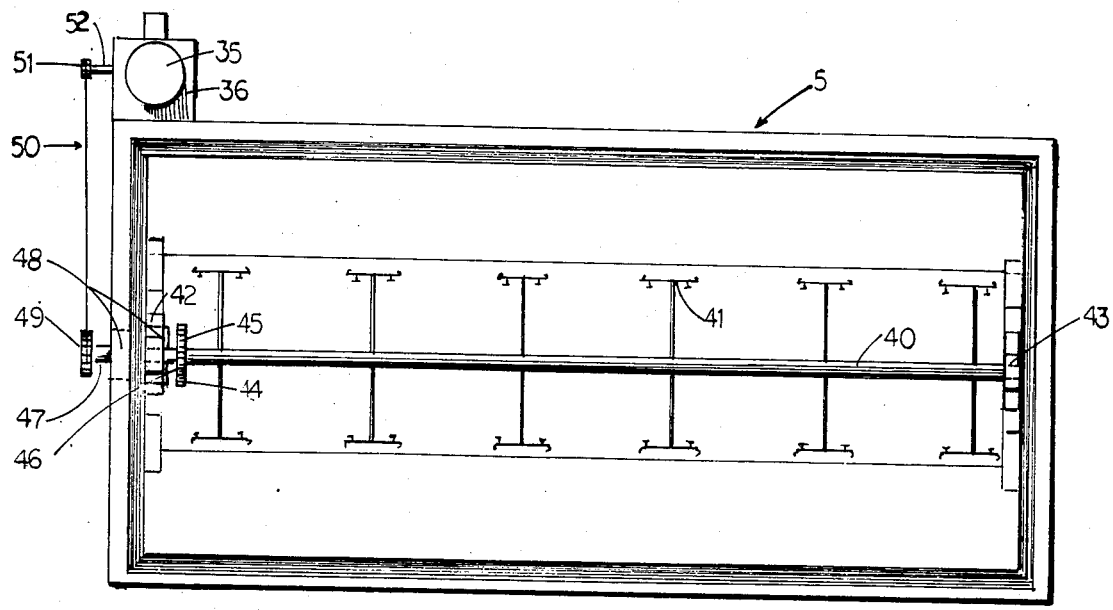
FIG. 8 is a top view of the tank base with the motor drive and elongated shaft containing sample mounting plates.

In FIG. 8, a top view of the tank base 5, the elongated shaft 40 containing the sample mounting plates 41 is shown with its bearing mounts 42 and 43. The elongated shaft 40 is rotated by a drive chain 44 inside the tank passing over a toothed sprocket 45 on the elongated shaft. The bottom inside sprocket 46 driving the chain 44 to the top sprocket 45 is hidden by sprocket 45 in this FIG. 8. The bottom inside sprocket 46 is mounted on a short shaft 47 extending through a liquid sealing bearing unit 48. The short shaft 47 at the tank liquid sealing bearing unit 48 bears sprocket 49 outside of the tank. The sprocket 49 is driven by a roller chain 50 which in turn is driven by a sprocket 51 mounted on the shaft 52 from the drive motor gear box 36 operated by the drive motor 35.

Figure 9:
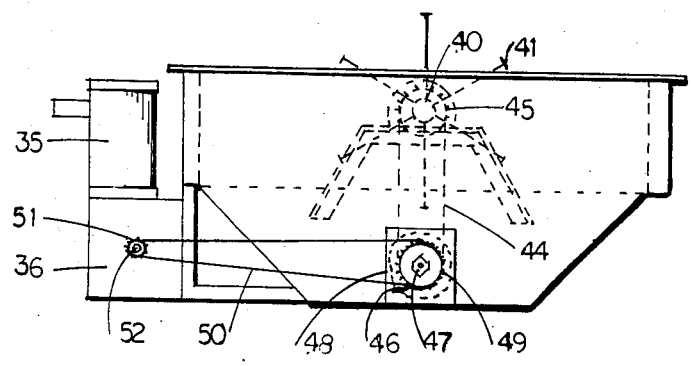
FIG. 9 is a side view of the tank base showing motor drive and chain drive of elongated shaft containing sample mounting plates.

In FIG. 9, the side view of the tank base showing the drive system, the drive motor 35 on the gear box 36 rotates the gear box shaft 52 bearing the sprocket 51 which drives the roller chain 50 on the outside of the tank. This chain 50 rotates the sprocket 49 on the shaft 47 passing through liquid sealing bearing unit 48 to the sprocket 46 (hidden by sprocket 49) inside the tank which drives the roller chain 44 and the upper sprocket 45 on the elongated shaft 40 causing it to rotate and to move the sample holders 41 into and out of liquid in the tank up to the infrared heater and past the fluorescent lamps before returning to the bath liquid.

Figure 10:
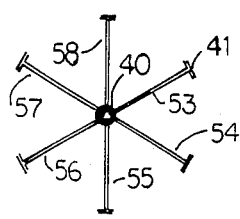
FIG. 10 is a side view of the cross section of the elongated shaft showing sample mounting spokes and sample holder mounts.

In FIG. 10 the elongated shaft 40 is shown in cross section with its attached sample mount spokes 53, 54, 55, 56, 57 and 58 holding sample mounts 41. Along the elongated shaft of FIG. 8 there are 6 sets of these spokes, thus, 36 samples can be accomodated in this configuration.

Figure 11:
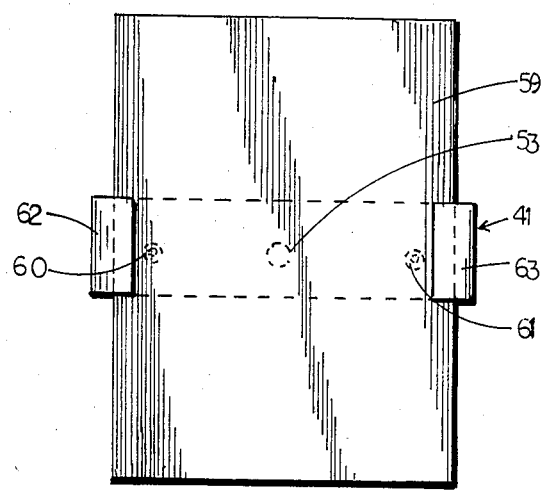
FIG. 11 is a front view of a sample holder mount with a sample in place.

In FIG. 11, a front view of a sample mount 41, a sample 59 is shown in place, secured by set screws 60 and 61, which press the sample against the turned edges 62 and 63 of the sample mount 41 which is secured to a sample mount spoke as exemplified by spoke 53.

Figure 12:
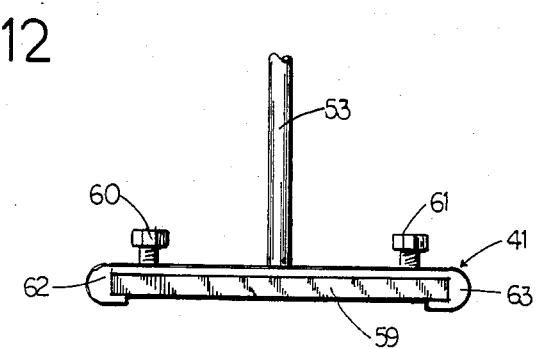
FIG. 12 is a top view of a sample holder mount with a sample in place.

In FIG. 12, a top view of sample mount 41, the sample 59 is shown held against the turned edges 62 and 63 of the sample mount 41 by the set screws 60 and 61 pressing the back of the sample 59. The sample mount 41 is attached to a sample mount spoke such as 53.

Figure 13:
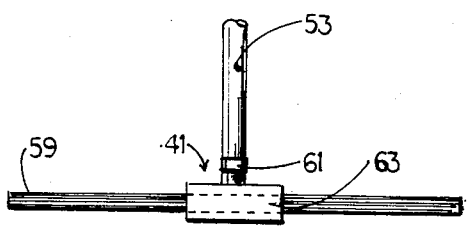
FIG. 13 is a side view of a sample holder mount with a sample in place.

In FIG. 13, a side view of sample mount 41, the sample 59 is held in place by set screw 61 pressing the back of sample 59 against turned edge 63 of the sample mount 41. The far turned edge 62 and set screw 60 are not visible. A sample mount spoke as exemplified by 53 is attached to the back of the sample mount.

Figure 14:
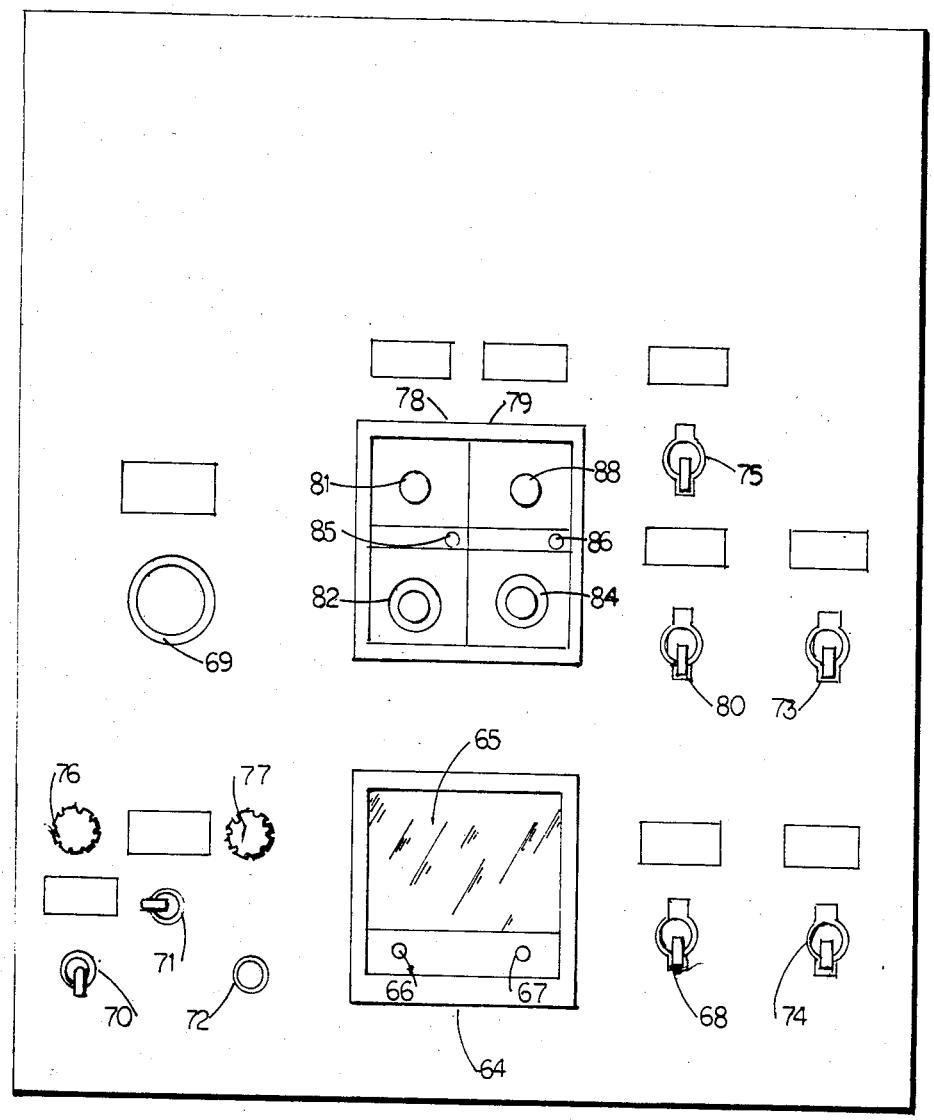
FIG. 14 is a front view of the control box.

In FIG. 14, a front view of the control box 2, the electrical controls and temperature readout of the test apparatus are depicted. The principal controls are those for the infrared heater, for the rotation speed of the elongated shaft with its sample mounts, for the time duration of run, for the time duration of pause and for the number of fluorescent tubes in operation.

The components of the front panel include an infrared heater digital indicating proportional controller 64 which displays the temperature sensed by the thermocouple 13 in the tank cover 4 as a digital display on panel 65 when switch 66 is in position. When the switch 67 is pushed, the display shows the set-point which has been entered. When switch 68 is in the UP position, power is supplied to the infrared heating element 14 if the controller 64 calls for heating.

The rotation speed is adjusted by the setting of the motor speed control 69 which operates when switch 70 for the rotation motor is pushed up. The direction of rotation is controlled by forward/reverse switch 71 which has 3 positions: forward, reverse and off. The pilot light 72 indicates when the drive motor is running.

In FIG. 14, switch 73 (UV #1) controls two of the fluorescent ultraviolet lamp tubes, and switch 74 (UV #2) controls two of the fluorescent ultraviolet lamp tubes. The ballast for the ultraviolet fluorescent tubes is mounted in the control box 2 and, when any pair of fluorescent tubes are turned on, the switch 75 for the cooling fan in the control box 2 should be turned on to cool the ballast units. In FIG. 14, of the two fuses 76 and 77 shown, fuse 76 protects the drive motor while fuse 77 protects the main power supply.

There are separate controls 78 and 79 for the run and pause time periods respectively. These controls are supplied power when switch 80 is moved in an UP position towards "rotating time" legend. The range indicator 81 in the "run" controller can be adjusted to six possible ranges of 1 second, 10 seconds, 1 minute, 10 minutes, 1 hour and 10 hours. The variable adjustment knob 82 (beneath the range indicator knob 81) sets the fraction of time that the run controller operates for the time range selected. A setting of 1.0 is 100%, while 0.5 is 50%. Thus, a range knob 81 selection of 10 minutes with variable control 82 at 0.25 would run for 2.5 minutes. The run control 78 controls the length of time that power is supplied to the drive motor 35 whose speed of rotation for the run period selected is controlled by control knob 69.

In this way the rate and extent of rotation of the elongated shaft carrying the samples can be closely set.

In like manner the pause control 79 has a knob 83 to select the pause period from within a range of 1 second, 10 seconds, 1 minute, 10 minutes, 1 hour and 10 hours. The variable adjustment knob 84 allows the selected range to be further subdivided in multiplier units of 0.1 from 0.1 to 1.0. The pause control 79 determines the length of the time period that drive motor 35 is not powered (i.e., it is turned off).

With adjustment of the "run" and "pause" controls, the rotation of the elongated shaft bearing the samples being tested can be widely varied. The "run" control 78, combined with the drive motor speed control 69, governs the rate and extent of rotation, while the "pause" control 79 governs the time period in which the rotation is stopped. Taken together these controls permit testing of a very wide range of exposure conditions where light exposure levels, temperature below infrared heater, water immersion temperature, and their temperature differentials (to be discussed later) are combined with time periods of "run" and "pause" and their differentials. For ease of observation of "run" and "pause" time periods, a pilot light 85 indicates "run" time, while pilot light 86 indicates "pause" time.

Figure 15:
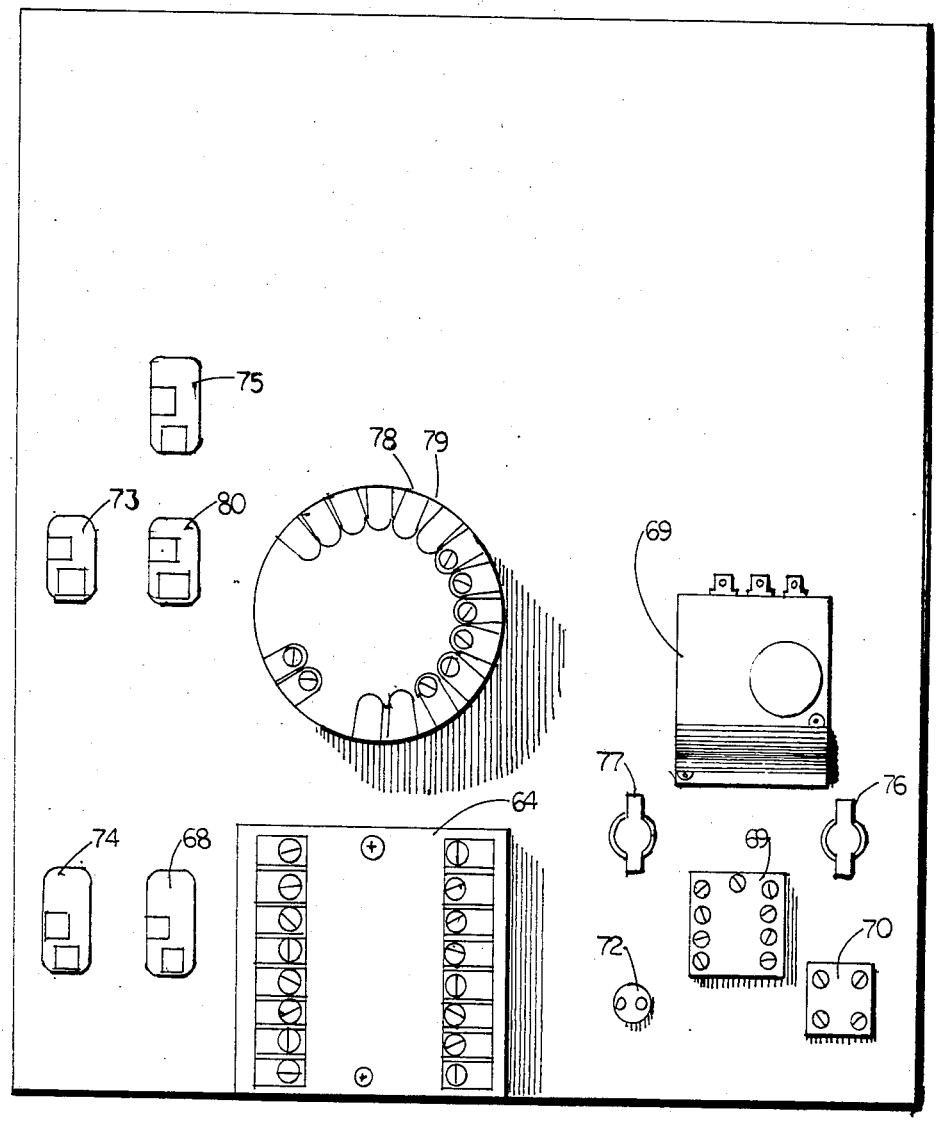
FIG. 15 is a back view of the front panel of the control box.

FIG. 15, a back view of the front panel of the control box 2, shows the rear view of the elements shown in FIG. 14 front view. This view shows the position of electrical connectors for wiring.

Thus the back of the motor speed control 69 is shown above fuse 76 for the drive motor circuit, and fuse 77 for the main power line. The switch 71 provides for direction of rotation control, while switch 70 provides power to the drive motor. The pilot light 72 indicates when the drive motor is running. The backs of "run" and "pause" controllers 78 and 79 are positioned above the infrared heater digital indicating proportional controller 64. The cooling fan switch 75 appears above switch 80 for power supply to "run" and "pause" controllers 78 and 79 which are offset above switch 68 for power supply to the infrared heater. The switches 73 and 74 control two fluorescent tubes each (UV #1 and UV #2 respectively).

Figure 16:
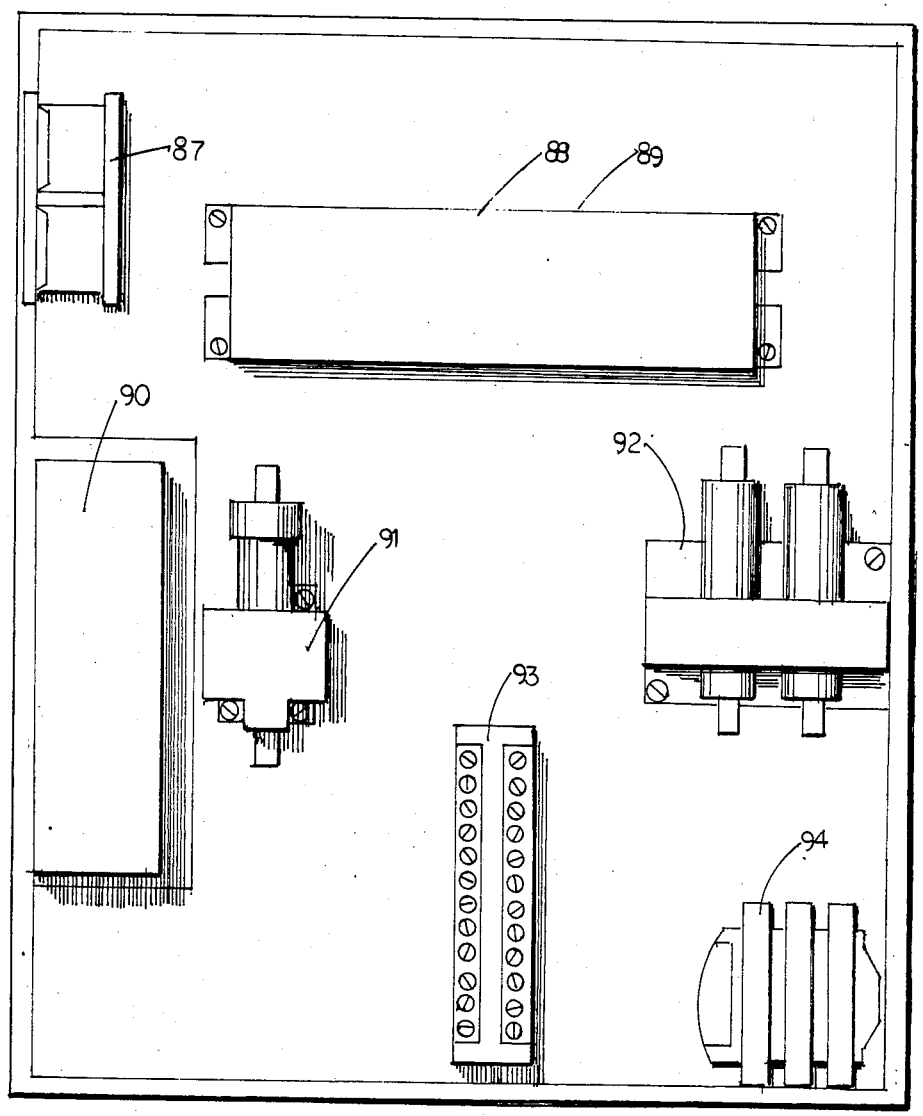
FIG. 16 is a front view of the interior of the control box.

FIG. 16, a front view of the interior of the control box 2, locates additional electrical components at the back of the control box 2.

The cooling fan 87 for the ballast units 88 and 89 (mounted one on top of another so that only 88 is visible) is operated by switch 75 of FIG. 14. The silicon rectifier 90 supplies DC power to the drive motor 35. A single mercury switch 91 controls 110 volt current, while a double mercury switch 92 controls 220 volt power. A terminal block 93 and a fuse container 94 complete the items in the back of control box 2.

Figure 17:
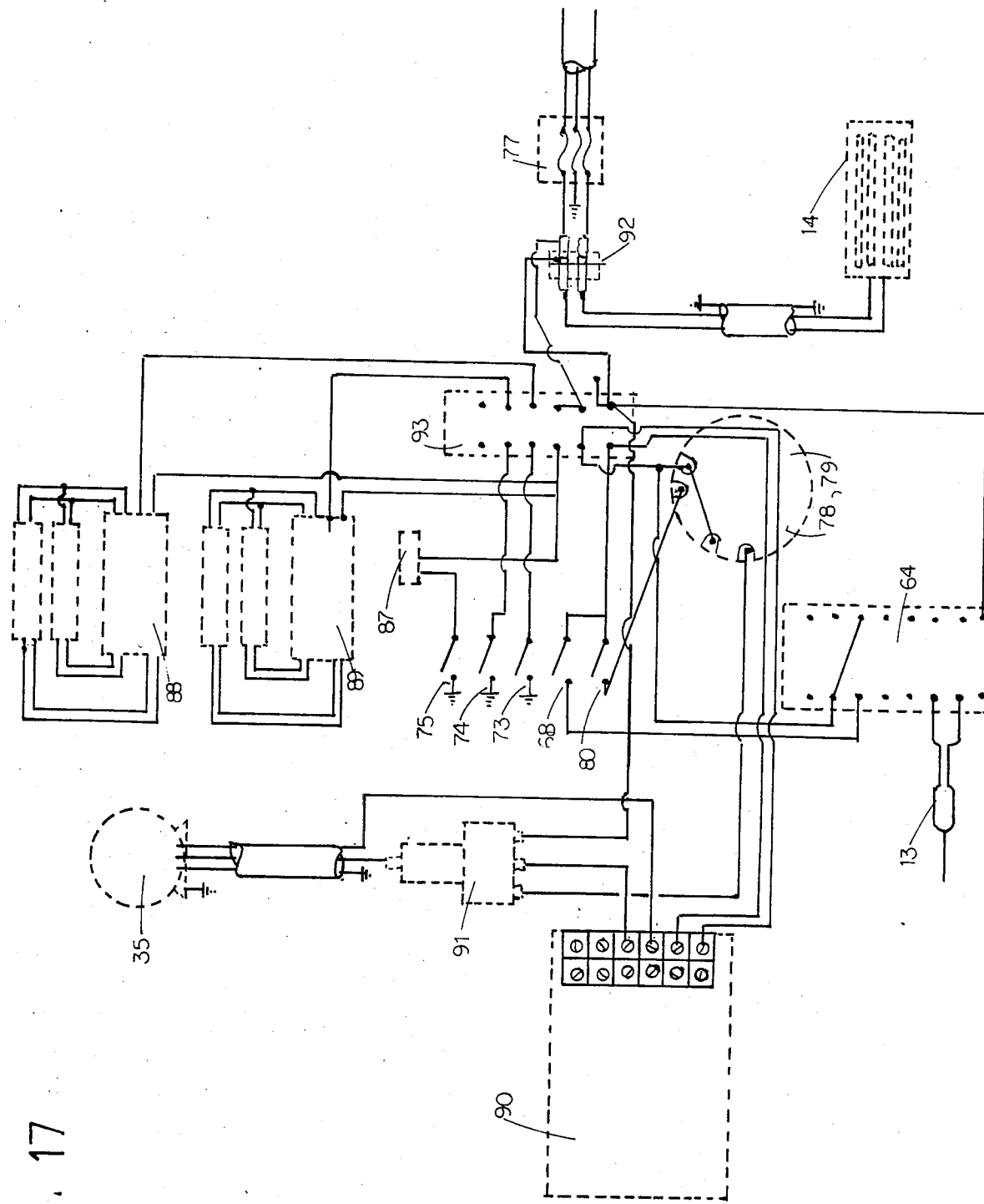
FIG. 17 is a wiring diagram of one possible embodiment of the test apparatus according to the present invention.

In FIG. 17, a wiring diagram of one possible embodiment of the test apparatus 1 and its control box 2, items are numbered to indicate their relation to the previous descriptions.

The operation of the test apparatus is illustrated by following the steps in conducting an exposure test on a sample. A sample 59 (see FIGS. 11, 12 and 13) which may be a panel bearing a coating to be tested or a panel whose composition or structure is to be tested, is mounted on the sample mounting plate 41. The moveable cover 4 (FIG. 1) is first raised by means of winch 9 by turning handle 10 to draw the wire rope 6 over the pulleys 7 and 8 and lift the attached cover 4. (The winch has a pawl or worm gear arrangement to hold the cover in whatever position is desired.) The elongated shaft 40 with sample mount 41 is exposed, and the sample is mounted on one of the 36 sample mounts. For ease of loading of the panels, there is a slip clutch installed as part of the drive chain bottom sprocket 49 on the outside of the tank base. This clutch nut is loosened to permit rotation by hand of the elongated shaft 40 allowing loading of test specimens in the sample mounts 41. After the unit has been loaded, the nut on the slip clutch is adjusted so that it will carry the weight of any unbalanced condition on the elongated shaft 40 and turn the unit without slipping. The slip clutch, however, is a safety device that prevents the shaft from turning should a sample 59 be dislodged and wedge between the bottom of the chamber and other test panels.

The sample 59 is mounted in the sample mount 41 by use of the set screws 60 and 61. If the sample is a metal or metal panel bearing a coating, the mounting is carried out in a manner to provide galvanic isolation from the set screws and the metal sample mount. This isolation is accomplished by using a dielectric material such as rubber or plastic to insulate the sample from the metal set screws and metal sample mount. A plastic tape may be placed around the sample to effect this isolation. Samples also should be loaded to provide a balanced condition on the elongated shaft 40. If two samples are mounted, one should be at a 12 o'clock position, and the second should be at a 6 o'clock position. One set of sample mounts should be filled along the length of the elongated shaft before another set of sample mounts is used for samples.

After the sample or samples are mounted, the tank base is filled with the immersion liquid to be employed. Most often this liquid is water containing salts, such as sea water or local hard waters. However, deionized water or water containing oil contaminants or soluble organic contaminants may be used. The bath liquid employed should represent (if possible) the immersion environment the sample is to encounter. The bath liquid obviously must not contain organic volatiles if air is employed in the vapor space because of the infrared heater and the risk of fire or explosion. However, an inert gas atmosphere (nitrogen, for example) may be employed in the vapor space to circumvent such hazards. The tank base is filled to a level to provide complete immersion of the rotating samples. This level is about the position where the sloping bottom of the tank base joins the base of the liquid seal well.

If desired, industrial gas contaminates (sulfur dioxide, for example) may be employed in the vapor space to test samples in such environments. After the samples are mounted and the tank base has been filled with the chosen water test liquid, the cover 4 is lowered into the liquid well which contains water or another liquid to effect a liquid seal. The winch 9 is employed in this step.

After the cover is lowered, the position of samples is noted through the viewing port as the elongated shaft is rotated slowly to make sure that samples do not touch the thermocouple beneath the infrared heater.

The tank base is set to establish the temperature of the water in the tank base. The gas for the vapor space is passed into the gas port.

Rotation of the elongated shaft carrying the mounted samples is started using the desired drive motor speed and the run time coupled with the desired pause time.

The desired number of fluorescent tubes are turned on with cooling for their ballast units.

The temperature of the infrared heater is set using the readout on the digital indicating proportional controller 64.

After the fluorescent tubes are turned on, eye protection should be used when observations are made through the viewing port to avoid ultraviolet irradiation of the eyes.

The test apparatus is set up to operate under the test conditions selected which would include selection of:

1. Tank bath composition.
2. Vapor space gas composition.
3. Temperature of infrared heater at thermocouple.
4. Temperature of tank bath composition.
5. The difference in temperature between 3 and 4 is used to establish the thermal shock obtained in operation.
6. Type and number of fluorescent tubes employed to supply irradiation.
7. Time period for rotation interval.
8. Rate of rotation.
9. Time period for pause interval.

10. Total exposure time in apparatus.

The conditions of immersion for absorption of bath liquids and of drying with light exposure for shrinkage during drying and for light degradation at elevated temperatures are established by the selection of 3, 4, 5, 6, 7, 8 and 9. The total exposure time in the apparatus determines the severity of the test in duration. Items 1 and 2 primarily affect corrosion and chemical attack.

The "pause" control setting establishes the time lapse over which no rotation occurs. For example, if it is desired to keep a test specimen in a certain position for 6 hours and then rotate it 180°, the "run" control should be adjusted to whatever time duration is necessary to rotate the rotating arm assembly 180°. This time interval must be established empirically by adjustment of drive motor speed and "run" time period. Next, the "pause" control should be set at 6 hours. In this mode, the rotational assembly will remain in a "pause" phase, after which it will rotate on the "run" phase for the time necessary to rotate the assembly 180° from the initial position. Again, there will be a 6-hour delay before the next 180° rotation—and so forth.

By adjusting the "run" and "pause" knobs, a variety of rotational performance can be attained. For example, with the elongated shaft configured for 6 rows of panels, each spaced uniformly around the circumference, the panels are separated by an arc of 60° from center to center. In order to have a uniform exposure within the apparatus and subject all panels to a thermal shock, a suggested rotational scheme might call for a rotation of 420° (1-1/6 revolutions). Thus, a panel in the 6 o'clock immersion position would be rotated out into the vapor phase, through the heat and light, and back into the immersion phase, but end up at the approximately 4 o'clock position (either totally or partially in immersion). During the next rotational phase, it would rotate again through the vapor phase and the immersion phase, but end up at the 2 o'clock position (in the vapor phase area).

The time and speed controls for running and the "pause" control allow exposure cycles in order to achieve tests designed for unusual exposure conditions as well as more normal exposure conditions.

The evaluation of samples may be carried out by comparing all the samples after a fixed duration of time in the test apparatus. Alternately, the samples may be observed (with eye protection) through the viewing port and the time recorded for approximately equal deterioration of samples. This latter method has the merit of establishing an estimate of the relative time scale of durability between samples.

This test apparatus is particularly useful in evaluating organic coatings on metal coupons where the thermal changes causing expansion and contraction, accompanied by fluid swelling and drying shrinkage, provide severe test conditions for organic coatings. Operation using brine or sea water baths allow one to observe samples for degradation by following corrosion in the samples. Primers beneath coatings as well as coatings can be evaluated in this manner.

In addition to coatings and primers on metal substrates, this test apparatus is useful in evaluation of composites. These composites often contain ceramic fibers, glass fibers, carbon fibers, graphite fibers, or rigid linear polymer fibers in a matrix polymer. This test apparatus subjects such composites to the conditions which frequently are most critical to their performance (water absorption and thermal changes under light irradiation).

Although coatings and composites are materials most likely to be evaluated by this apparatus, polymers also are advantageously tested on this apparatus, especially polymers which contain impact modifying agents such as ABS resins, impact modified nylons, and impact modified polyacetals. Film laminate systems are effectively tested in this apparatus as well as building material laminates and composites.

Natural products such as wood and including adhesives and coatings on such products can be tested. While this test apparatus is useful for single material systems, it is of especial value in conducting tests on samples containing more than one material where the test conditions of immersion and drying, thermal expansion and contraction, conducted in the presence of light, accentuate any differences in the moisture absorption or thermal expansion or light stability of materials of multi-component systems.

In order to achieve a constant temperature differential between the temperature of the thermocouple below the infrared heater strip, which heater strip the test samples approach during drying, and the temperature of the tank base with its aqueous test liquid in which the samples are immersed for cooling and for water absorption, the tank base is provided with means by which the aqueous test liquid in the tank base can be maintained at a constant temperature. The temperature differential between the thermocouple beneath the infrared heater and the aqueous test liquid in the tank base thus is held constant.

It is obvious that the infrared heater and, to a lesser extent, the fluorescent lamp tubes supply heat to the aqueous test liquid in the tank base. This excess heat from the aqueous test liquid must be removed in order to maintain the aqueous test liquid at a constant temperature. The liquid in the tank base may be maintained at a constant temperature by any one of a number of methods.

These methods involve removal of heat by circulating the aqueous test liquid through an external heat exchanger or by heat exchange with the tank base and with the tank base being cooled by a separate liquid flow stream or by gas flow against the tank base.

With any of these systems the tank base usually is provided with a thermocouple added through a Tee to the tank drain opening 39. The output from the thermocouple is employed in a control circuit to maintain the tank test liquid at a constant temperature. For example, the test liquid may be pumped from the tank base through the open arm of the Tee bearing the tank thermocouple, through tubing formed into a coil which is immersed in a constant temperature bath, and from the immersed coil back to the filling opening of the tank base. The thermocouple output may be employed to signal operation of the pump in this cooling circuit. When the test liquid temperature is low enough, the thermocouple stops operation of the pump. Alternately the pump may be operated continuously, and the tank base thermocouple signal may be used to lower the temperature of a circulating bath around the coil heat exchanger to remove additional heat. When the test bath liquid is sufficiently low, the thermocouple stops further cooling.

While the test liquid is usually circulated through a heat exchanger external of the tank and back to the tank, the tank test liquid also may be maintained at a constant temperature by closing the fill and drain openings, but with a thermocouple in place in one of the openings.

If the desired test liquid temperature is not too low, the thermocouple signal from the temperature of the tank test liquid may be utilized to activate a fan blowing cooling air on the tank base external surfaces.

The thermocouple signal from the temperature of the tank test liquid could also be used to open a solenoid to provide cooling liquid to a jacket on or around the tank base.

Such a liquid may be supplied from a separate constant temperature circulating liquid system, or this liquid may be water supplied from municipal water mains having a relatively constant low temperature. The temperature in the tank base liquid usually is above 0° C., but it may be held below 0° when the aqueous test liquid is sea water or water containing an anti-freeze liquid such as ethylene glycoL and a suitable cooling liquid is used for heat exchange.

While heat transfer will most often be carried out to withdraw the heat from the aqueous test liquid, on occasion when a higher temperature in the aqueous test liquid is desired, no heat transfer means need be employed. The tank base aqueous test liquid will rise to a temperature balanced by heat transfer to room temperature in the air around the test chamber. The thermocouple in the tank base can be employed to record the equilibrium temperature.

At times, for special tests, it may be desirable to circulate heat transfer liquid which is above room temperature or to circulate bath test liquid through a heated coil in order to determine the effect of sample ixmersion in warm aqueous test liquid at a constant temperature.

The heat transfer means incorporated in the tank base may be any suitable means such as coils or plate-coils or channels in the metal of the tank base or a liquid chamber with baffles next to the metal of the tank base.

The heat transfer means may be accomplished by external liquid flow through a serpentine path of coils bonded to the bottom half of the tank base. This arrangement is simple and provides means for establishing a relatively wide range of constant cooling temperatures in the tank base when a liquid at constant temperature is passed through the coils.

The thermocouple in the tank base side wall lies in the aqueous test liquid parallel to the tank bottom, and, when the temperature of the liquid in the bath is above the desired bath liquid temperature, a controller opens a solenoid valve to allow cool heat transfer liquid to flow through the heat exchanger to cause the bath liquid temperature to drop. When the desired bath liquid temperature is reached, the controller on input from the thermocouple in the bath liquid causes the solenoid to close and stop the flow of cool heat transfer liquid to the heat exchanger in the bottom of the tank base. The aqueous test liquid has its temperature maintained at a desired level by this means.

This test apparatus is designed for service in corrosive environments. The cover and tank base and elongated shaft with its interior sprockets and drive chain are fabricated of stainless steel or another corrosion resistant metal. For corrosion resistance 316 stainless steel normally is employed.

The inside walls of the cover and the upper walls of the tank base are normally polished to obtain as high a reflectance of light energy as possible with the metal or other material employed in its construction.

For especially corrosive test conditions, other metal systems including nickel and tantalum or their coatings on steel may be employed as well as special alloys such as Hastelloy C. If necessary, glass or ceramic coatings on metal may be employed for especially corrosive environments. In severe environments it may be necessary to enclose the infrared heater in glass as well as the fluorescent tubes with their tube and mountings. The glass selected to enclose the infrared heater would be chosen to transmit as much infrared as possible, and the glass selected to enclose the fluorescent tubes and their end connectors would be chosen to transmit as much ultraviolet as possible.

The liquid employed in the liquid seal well normally is water. However, other liquids, including inert oils such as mineral oil or silicone oils, might be employed. In some circumstances mercury could be employed when the test room is well ventilated.

The fluorescent tubes employed normally are 40 watt 48 inch long tubes which are capable of emitting intense ultraviolet light. While fluorescent tubes providing visible and infrared energy as well as ultraviolet can be used, the fluorescent tubes providing a significant percentage (greater than 5 percent) of ultraviolet light of wavelength less than 4000Å are preferred.

The control instruments in the control box unit have been described in terms of their function. The infrared heater and fluorescent tubes have also been described in terms of their function. While any source of such units may be employed, the following specific units have been employed:

Infrared heater with reflector was supplied by Edwin L. Wiegand Division of Emerson Electric Company under tradename of "Chromalox".

Fluorescent tubes were supplied by Westinghouse as Ultraviolet Sunlamp FS 40 tubes.

Digital Indicating Proportional Controller was supplied by Chromalox Instruments and Controls Division of Emerson Electric Co.

Timing "run" and "pause" controls were supplied by (atc) Automatic Timing and Controls Co., King of Prussia, Pennsylvania 19406, under Catalog 342 Flip-Flop Cycle Timer.

The thermocouples employed were K type with armor shield tubes.

These electrical components are connected in a manner to perform the functions described in this disclosure and consistent with manufacturers' recommendations for installation of the units and consistent with electrical safety code practice. The wiring diagram employed should be laid out by one skilled in the art to satisfy the above requirements.

Modifications and variations of the present invention are possible in light of the above description and teachings of this disclosure on this test apparatus. A number of examples of such modifications and variations have been delineated in this disclosure.

We claim:

1. Apparatus for testing samples of materials under controlled exposure conditions, said apparatus comprising:

a two part corrosion resistant chamber, said chamber having a tank base with a liquid seal perimeter well and said tank base of said chamber adapted to contain an aqueous test liquid, and said chamber supplied with a moveable cover having mounted inside of said moveable cover an infrared radiant heating strip with a thermocouple extending beneath said radiant heating strip and with elongated fluorescent lamp tubes also mounted inside said cover and with said cover having a viewing port on said cover and with said cover possessing a gas inlet port at an end of said cover and a gas outlet port at opposite end of said cover;

a frame for mounting said tank base of said chamber and means for lifting said cover from said tank base;

a horizontal elongated, rotatable shaft mounted lengthwise within said tank base and enclosed by said moveable cover when said moveable cover rests on said liquid seal perimeter well of said tank base and with said elongated rotatable shaft having spokes extending outward from said shaft on which said spokes are attached mounts for holding test samples on said mounts and with said elongated rotatable shaft being rotated by a drive train from a motor with said motor having its speed controlled by an adjustable controller and with said motor having its "run" time controlled by an adjustable timer and with said motor having its "pause" time controlled by a separately adjustable timer;

means for energizing said fluorescent lamp tubes;

means for energizing said infrared heater strip and means to measure and set the temperature level beneath said infrared heater;

means to energize said drive motor and means to control speed of said drive motor;

means to control length of time said drive motor "runs" before "pausing";

means to control length of time said drive motor "pauses" before "running";

means to measure and set temperature level of test liquid of said tank base;

said mounting of said sample on said elongated rotatable shaft allowing exposure of said sample to immersion in a temperature controlled aqueous test liquid, heating and drying of said sample rotated out of said aqueous test liquid in a controlled atmosphere vapor space beneath temperature controlled infrared heating strip, irradiation of said sample by further rotation adjacent to said fluorescent lamp tubes, cooling said sample by further rotation to effect immersion in said aqueous test liquid with said controlled temperature, said rotation period being stopped for a "pause" before said rotation is resumed for a "run" period.

2. The apparatus of claim 1 wherein radiation source is formed of a plurality of elongated fluorescent lamp tubes emitting more than 5% of the total radiation as light with a wavelength below 4000Å.

3. The apparatus of claim 1 wherein said tank base is provided with means to add or withdraw aqueous test liquids.

4. The apparatus of claim 1 wherein lifting of said cover from said tank base is accomplished by means of a wire rope passing over pulleys to a winch for winding said wire rope upon its drum.

5. The apparatus of claim 1 wherein the said drive train from the said motor to the said elongated rotating shaft is comprised of sprockets and drive chains and one set of which is located outside said tank base and the second set of which is located inside said tank base with a common shaft from each set passing through a bearing with sealing rings and with said bearing mounted on the end wall of the tank base.

6. The apparatus of claim 1 wherein the drive train from the drive motor to the elongated rotating shaft contains an adjustable slip clutch within the said drive train.

7. The apparatus of claim 1 wherein the said infrared heating strip is mounted beneath a reflector for infrared energy.

8. The apparatus of claim 1 wherein the said two part corrosion resistant chamber possesses polished walls which reflect radiant energy.

9. The apparatus of claim 1 wherein controls for said infrared heater temperature, said fluorescent lamps and their ballasts, said drive motor speed, said "run" and said "pause" time period controllers are mounted in a cabinet separate from said moveable cover and said tank base, and with air cooling means provided to said cabinet by a fan and with said cabinet electrically connected by cables to electrical components of said moveable cover and said tank base.

10. The apparatus of claim 9 wherein controls for said aqueous test liquid temperature are mounted in said cabinet.

* * * * *